United States Patent [19]
Dales et al.

[11] Patent Number: 5,352,205
[45] Date of Patent: Oct. 4, 1994

[54] BLOODLESS INSERTION CATHETER ASSEMBLY

[76] Inventors: Lawrence Dales; Elsa A. Dales, both of 1556 Old Orchard St., West Harrison, N.Y. 10604

[21] Appl. No.: 121,706

[22] Filed: Sep. 16, 1993

[51] Int. Cl.$^5$ ............................................ A61M 5/00
[52] U.S. Cl. .................... 604/158; 604/165; 604/168
[58] Field of Search .............. 604/158, 164, 167, 165, 604/168, 256, 198

[56] References Cited

U.S. PATENT DOCUMENTS

| | | | |
|---|---|---|---|
| 4,613,329 | 9/1986 | Bodicky | 604/158 |
| 4,654,031 | 3/1987 | Lentz | 604/168 |
| 4,867,745 | 9/1989 | Patel | 604/158 |
| 5,092,845 | 3/1992 | Chang | 604/158 |
| 5,098,395 | 3/1992 | Fields | 604/168 |
| 5,120,319 | 6/1992 | Van Heugten et al. | 604/168 |
| 5,256,148 | 10/1993 | Smith et al. | 604/158 |

*Primary Examiner*—Paul J. Hirsch
*Attorney, Agent, or Firm*—Martin J. Spellman, Jr.

[57] ABSTRACT

A catheter assembly having a catheter of flexible plastic tubing secured at one end to a catheter hub, a hollow adaptor body with a distal end for fluid tight connection to the catheter hub and in fluid communication therewith. The proximal end of the adaptor body includes a self closing elastomeric gasket valve member. An introducer needle is provided proportioned to extend through the catheter, hub and tubing for penetration of a patient's vein for introducing the catheter into the vein. The proximal end of the needle is secured to a plastic collar having proximal and distal ends and dogs at the proximal end for limiting slidable movement within a hollow cylindrical container. A sealable gasket closure at the distal end of the container safely encloses the needle within the container upon withdrawal of the needle. The assembly further includes a curved plastic transparent tube having a filter valve therein extending from the proximal end of the collar for sighting flashback. The valve allows air flow but prevents fluid flow. An adaptor unit connects to the hub, the adaptor unit having a hollow shaft with a sharp end, and ports on its side walls. The shaft is proportioned to pierce said gasket valve member in the adaptor body to place the adaptor body and the adaptor unit in flow communication.

2 Claims, 4 Drawing Sheets

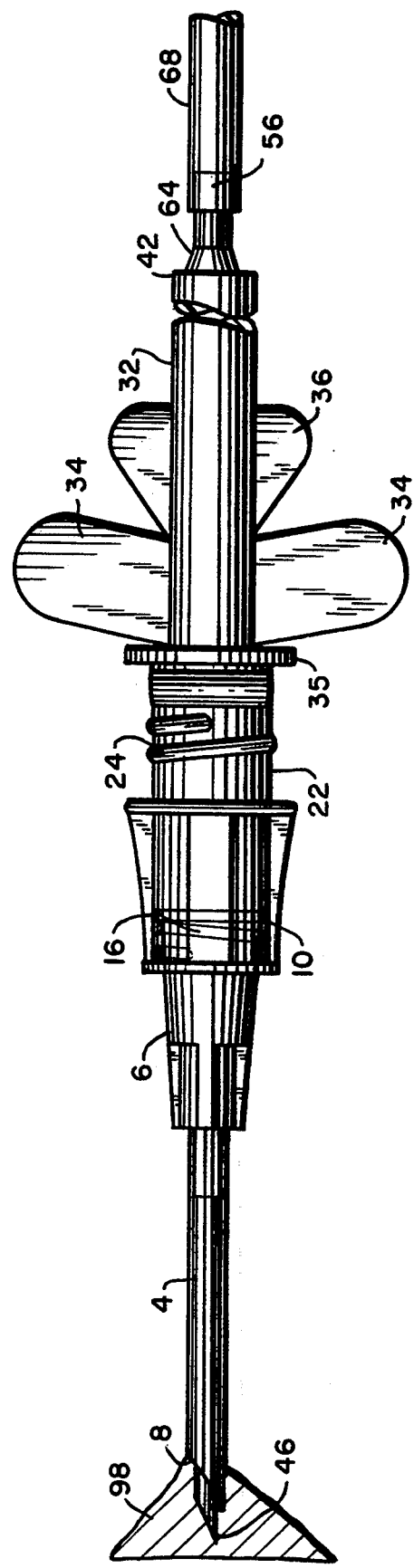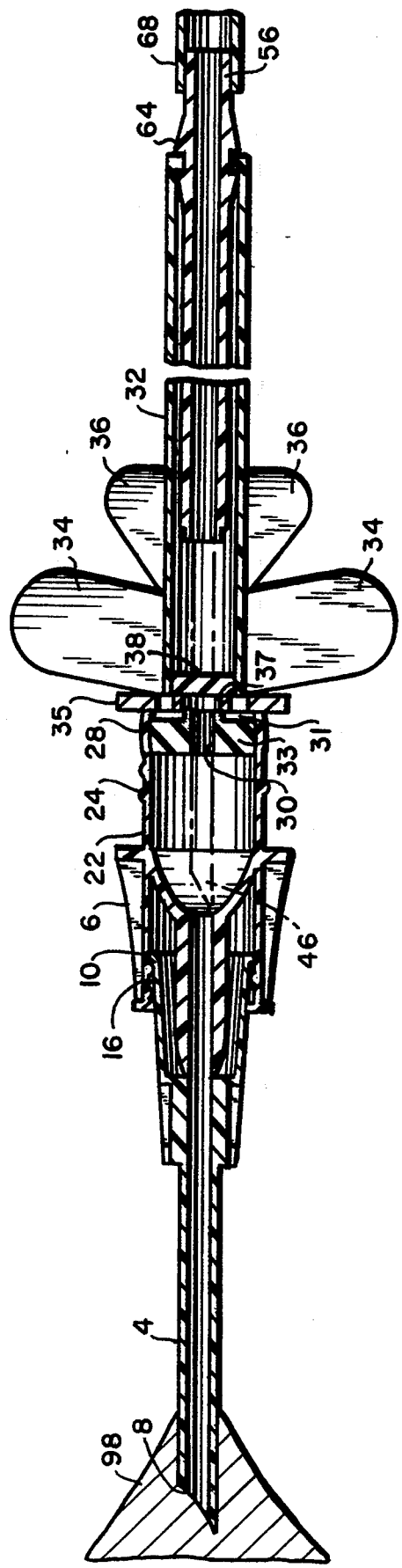

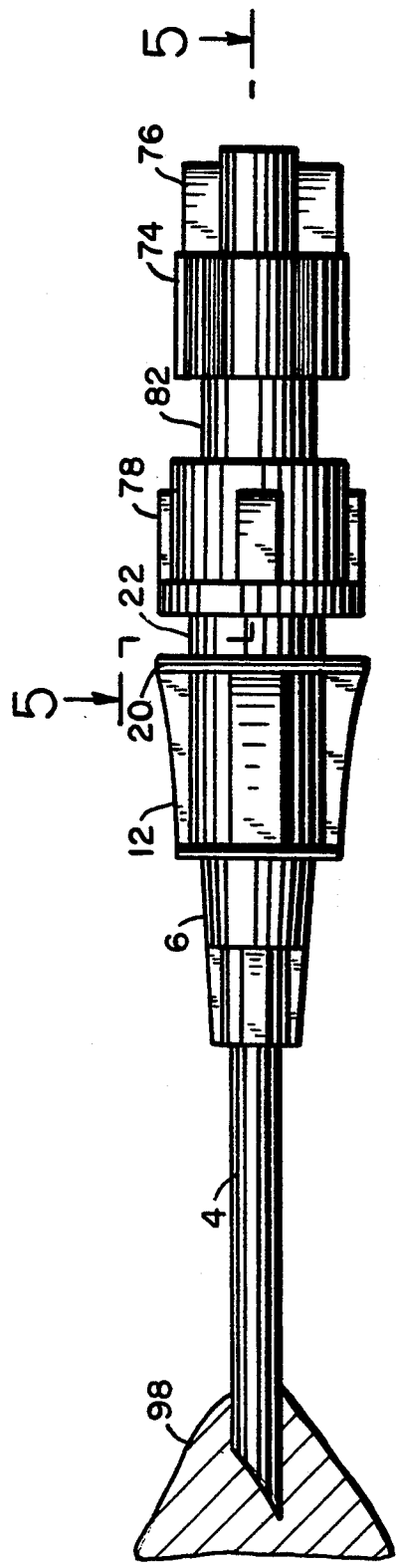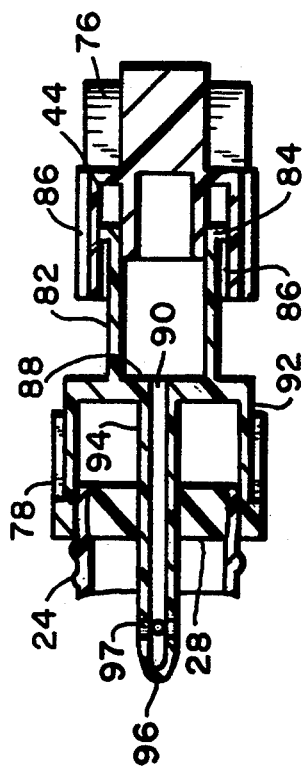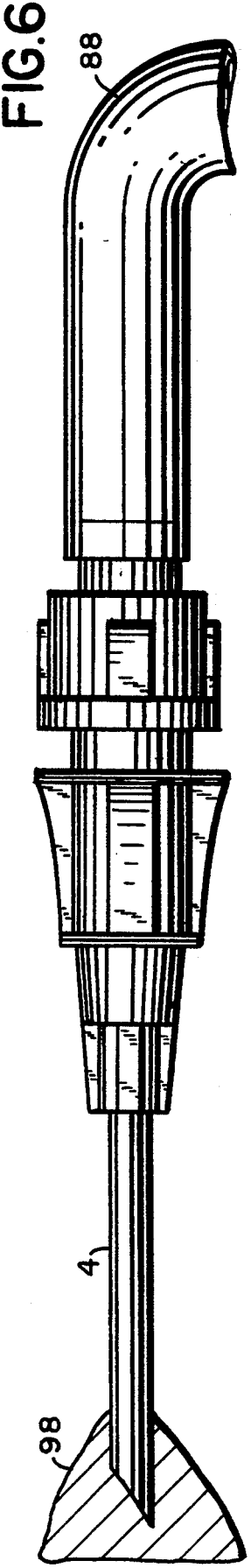

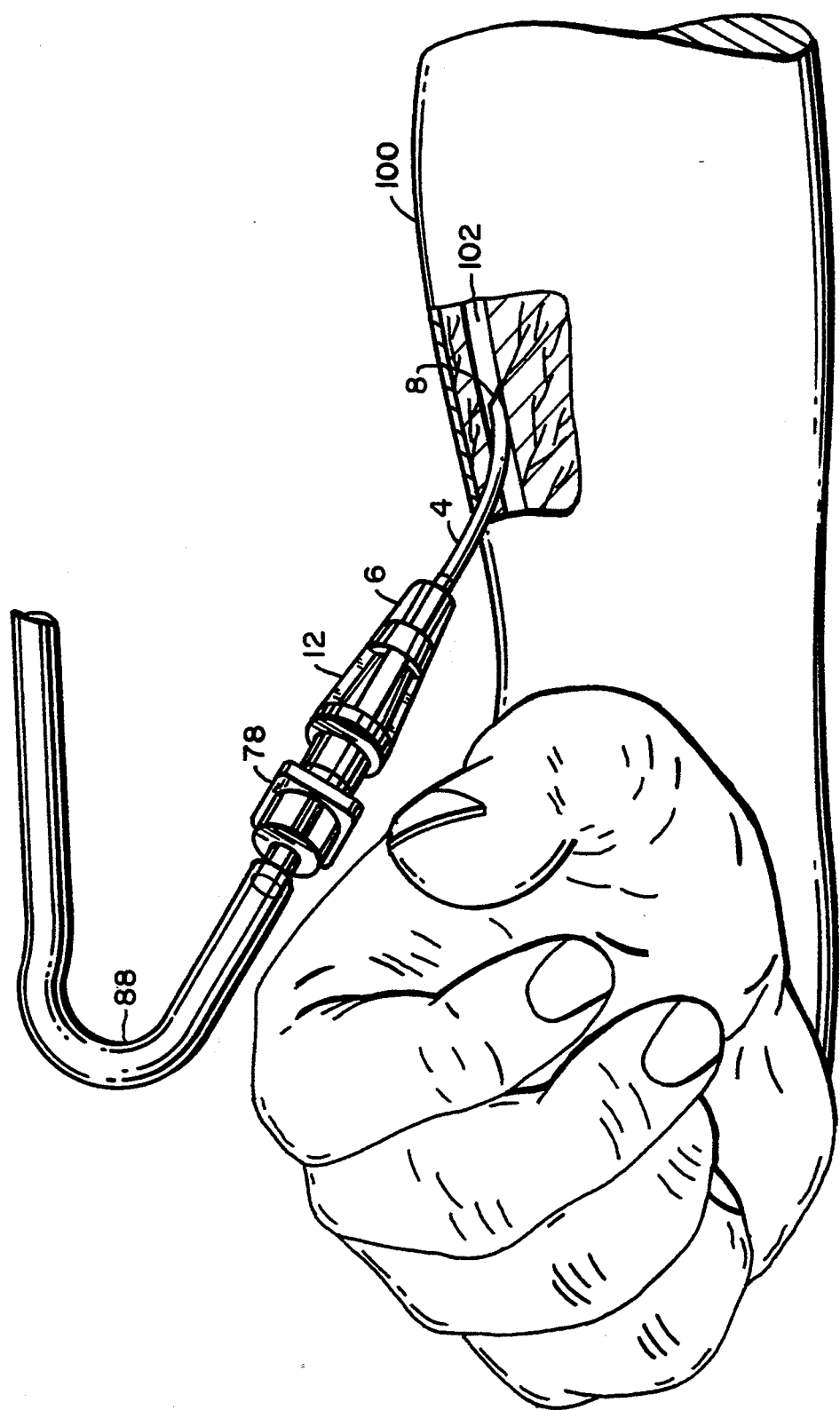

BLOODLESS INSERTION CATHETER ASSEMBLY

BACKGROUND OF THE INVENTION

1. Field of the Invention

This invention is concerned with a bloodless insertion catheter assembly to insert a catheter in a patient generally for the purposes of administering nutrients or medications through an IV supply tube.

The insertion of a catheter into the vein of a patient and the withdrawal of the inserting needle and attachment of IV tubing up to the present time has presented significant dangers to the administering medical personnel. Exposure to patient's blood can infect the medical personnel with AIDS and other serious blood borne diseases such as hepatitis.

The usual insertion procedure involves inserting a needle through the catheter into the patient's vein, advancing the catheter into the vein, and then withdrawing the needle. As the needle is withdrawn, there is a danger of contact with the patient's backflow of blood. Also, when the needle is withdrawn from the catheter apparatus, there is a danger of the user being accidentally pricked with the needle. The danger of backflow of blood from the catheter when the IV tubing is attached to the external end of the catheter is a very serious concern. Various attempts to minimize these dangers have generally concentrated on means to eliminate accidental needle sticks and to a lesser extent minimizing the danger from the return flow of blood. There is no device presently available, however, which is simple in construction and which, in an easily utilized procedure, eliminates the danger both of needle stick and the contamination by back flow of the patient's blood from the catheter during connection and disconnections of IV apparatus.

The device of the present invention also provides a means for insuring access has been gained to the vein by easily viewing the backflowing blood.

The present assembly also automatically entraps the withdrawn needle and provides a completely safe way of preventing the backflow of blood, and for the attachment of the IV apparatus to the catheter.

A further concern, eliminated by this invention, is the possible inadvertent contamination of the catheter hub interior upon withdrawal of the introducer needle by the nurse.

2. Prior Art

In U.S. Pat. No. 5,088,984 Fields, discloses a medical connector for intravenous fluid carrying tubes comprising a pair of connector members, one of which carries a rubber septum that is penetrated by the needle when the first and second members are joined, establishing flow communications through the needle to a flash back chamber. A one way valve prevents the patient's blood from entering a flashback chamber but allows for communication through the needle.

U.S. Pat. No. 5,013,304, Russell utilizes protective sheath for a needle after being withdrawn from a catheter, and a backflow device to reseal and prevent discharge of the blood upon withdrawing of the needle.

U.S. Pat. No. 3,097,646, Scislowicz shows an apparatus where the needle punches the vein and then is withdrawn, sealing in the blood beyond the seal. The flexible tubing or catheter remains in the vein and the blood is seen through the clear tubing. No means of withdrawing the needle in a safe manner is shown and the IV apparatus utilizes a second needle to punch the seal in order to connect the IV material with the catheter. There is no needle retraction cover.

Other patents of background interest are:
U.S. Pat. No. 4,758,225, Cox; U.S. Pat. No. 5,171,231, Heiliger; U.S. Pat. No. 5,137,515, Hogan; U.S. Pat. No. 5,154,703, Bonaldo; U.S. Pat. No. 5,171,324, Japson et al.

SUMMARY OF THE INVENTION

The new apparatus system of the present invention completely seals off the catheter preventing the backflow of blood from spilling before the IV tubing is connected. A uniquely designed connector adapter is provided for connecting the IV to the catheter, preventing any spillage of blood in combination with an insured means of securing the withdrawn inserter needle and its blood contents and sliding tube.

The system, aside from protecting the health care workers by preventing the spillage of return flow of blood, which also can be unsettling to the patient, guards against accidental needle sticks in a conveniently usable and readily manufactured assembly.

The device includes a standard flexible plastic catheter of appropriate length and with an inside diameter to conform to the insertion needle used. The proximal end of the catheter is fused to a standard male catheter base for insertion into the LUER LOK of a catheter retainer which incorporates an access valve. This latter unit is made of transparent plastic and has a standard female LUER LOK socket at the proximal end for retention of the catheter hub.

The catheter hub and access valve body may be constructed as a single unit, however, it is preferable they be constructed separately so that in the event of contamination or malfunction of the latter unit, it could be separated from the catheter and replaced without the necessity of removing the catheter from the patient and having to insert again at a different site.

Central longitudinal passages through the connector are of appropriate diameter and sufficient length to allow for the free, but controlled passage of the insertion needle and subsequent freeflow of IV fluids to be delivered to the patient through the catheter.

An elastomeric diaphragm in the form of a silicone rubber gasket at the distal end provides a self sealing access channel in its center for the insertion of the insertion needle and the adapter connector as described below.

The gasket is designed for easy access by the needle and the IV adapter. When either of these is withdrawn, the gasket prevents the backflow of blood from the patient beyond this point and also during any subsequent attachment or detachment of administration apparatus. Preferably the external surface of the silicone gasket is covered with a crimped metal retainer and optionally a guide to properly place the needle or connecting apparatus for easily locating the access channel in the gasket or connections for the adapter unit.

The proximal end of the insertion needle is fused to a transparent plastic flexible tubing which serves as a flashback chamber for verification of the return of blood. This tubing protrudes from the rearward end of a needle retention cylinder to allow for the observation of the presence of blood and also to be utilized for grasping between the fingers to serve as a handle to pull to retract the needle and to retain it in the security of a plastic retention cylinder. The connection between the needle and this tubing is covered with a plastic collar which serves as a seal between the connector and the inside diameter of the protective cylinder. The collar has dogs which are compressed within the cylinder and, upon completed retraction, engage the rear of the cylindrical container to prevent further retraction or reemergence of the needle.

The cylindrical plastic collar is utilized to enclose the metal needle upon retraction as well as the connecting IV tubing to the needle.

The rear or proximal wall of the cylinder container closes around the needle collar to engage the dogs upon full retraction to prevent further longitudinal movement of the needle either forward or backward. Attached to the sides of the outside cylinder are two pairs of wings that are designed to afford contact for finger pressure during the insertion/retraction process and lie flat against the surface of the patient's skin.

The adapter at its distal end is provided with an extending cylindrical channel over the end of which the IV tubing is attached. The distal end is provided with an internal LUER LOK threading for connection to the catheter hub proximal end. Within a central axis of a cavity is a hollow tube closed at its front end with a sharp shaped point to penetrate the sealing gasket. It has access ports along its side walls to allow the passage of fluids from the tubing into the chamber. The sharpened point is inserted through the access port in the gasket and secured in place by engaging the LUER LOK threadings. Thereafter the infusion can be performed with fluids flowing through the tubing, the adapter fitting into the flush chamber of unit base and through the catheter to the patient's blood stream.

In use, the assembly is utilized in the usual manner by inserting the needle followed by the catheter into the appropriately chosen IV site.

The transparent tubing with the filter valve at its outer end is viewed as a flash back chamber for the confirmation of successful venous access.

Thereafter, an optional push-off ring, and/or the wings of the cylinder are utilized to withdraw the introducer needle from the catheter.

The transparent tubing is grasped and pulled rearwardly to retract the introducer needle into the cylindrical chamber wherein it is safely retained by a sealing gasket at the front or distal end of the chamber and the dogs at the end of the plastic casing engaging the rear or proximal wall of the cylindrical chamber.

Preferably the distal end of the cylinder unit has a "locking gasket" so that once the needle is safely within the cylindrical chamber, it may not be advanced and any backflow of blood is confined to the connecting chamber of the second unit due to the self sealing gasket upon withdrawal of the needle.

The catheter and the connector are then secured to the patient.

Thereafter the adapter connector is connected with its IV tube having been previously connected at one end and the flow is established.

BRIEF DESCRIPTION OF THE DRAWING

In the accompanying drawing which forms a part of this specification:

FIG. 2 is a plan view of the assembly being utilized for insertion into the patient's infusion site;

FIG. 3 is a sectional view with the catheter inserted and the needle being withdrawn from the patient and catheter;

FIG. 4 shows the catheter and catheter hub with the adapter unit and cap in place on the proximal end of the catheter hub and in flow communication with the interior of the catheter hub;

FIG. 5 is a sectional view taken along 5.5 of FIG. 4 showing the interior of the adaptor unit connector and sealing valve;

FIG. 6 is a plan view of the unit as shown in FIGS. 4 and 5 with the end cap of the adaptor unit removed and the IV tube connected to the adapter connector; and FIG. 7 is a perspective view, partly cut away, showing a unit as shown in FIG. 6 in place for infusion of IV materials into patient's vein.

ILLUSTRATIVE SPECIFIC EMBODIMENT

Figure 1:
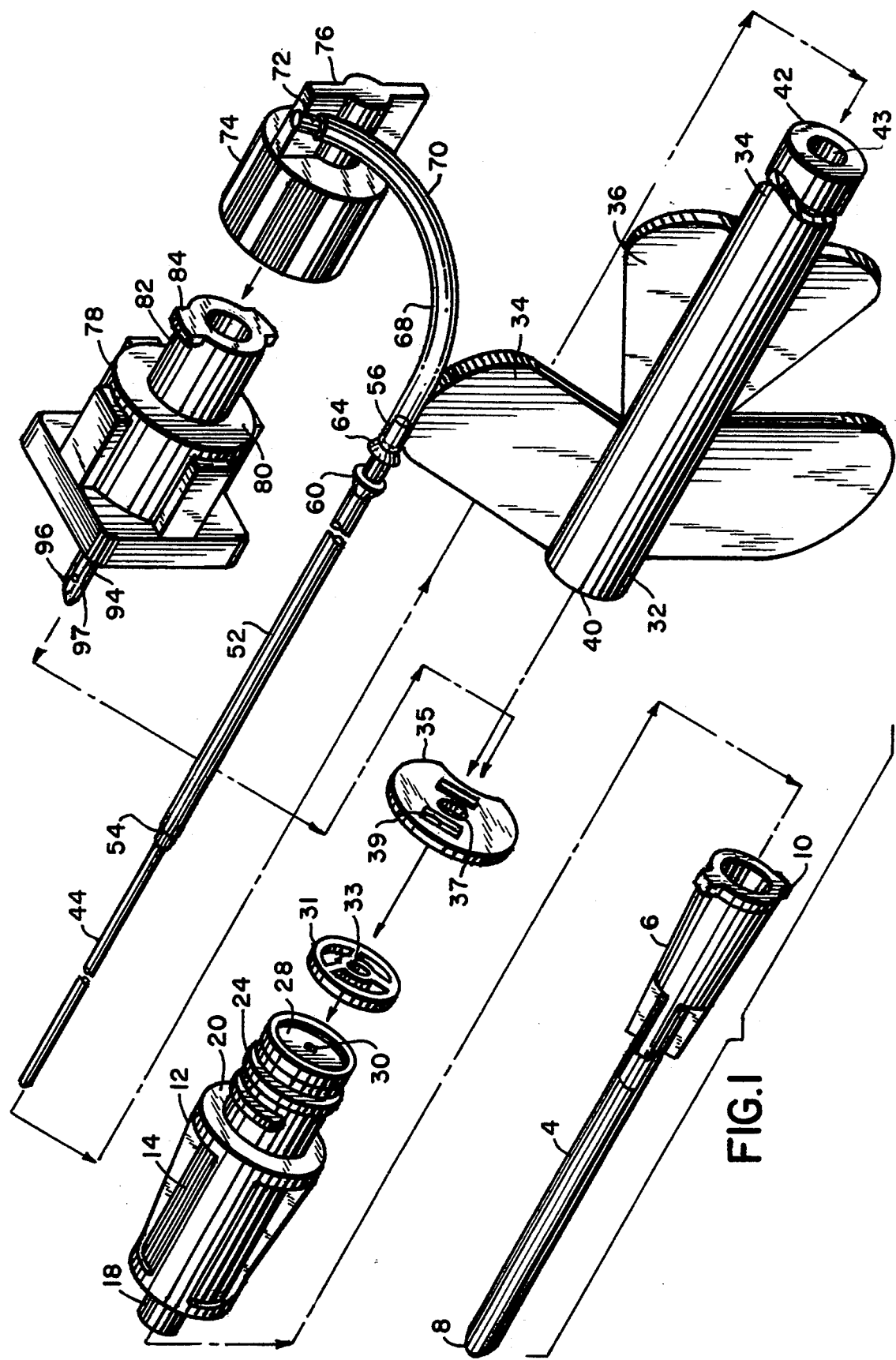
FIG. 1 is an exploded view of the assembly showing the individual components separately.

An example of a bloodless insertion catheter assembly is illustrated in the accompanying drawing wherein the numeral 2 indicates the assembly in general.

Assembly 2 comprises a conventional flexible plastic catheter 4 secured to a catheter hub 6. The distal end 8 of the catheter 4 is beveled where the penetrating introducer needle 44 joins it in sliding relationship in the usual manner. The hub 6 is secured to the catheter retainer body 12 by turning the hub 6 clockwise so that the nubs 10 of the hub 6 interlock with the internal LUER LOK threads 16 of the body 12. The hollow cylindrical channel 18 extends from the distal end of the body 12, and fits snugly with the internal tapered channel 19 of the catheter hub 6. It is drawn tightly by the twisting action of the LUER LOK threads 16 on body 12 and the nubs 10 of the catheter hub 6. Ledge 20 is provided for assisting in pushing or controlling the insertion of the catheter into the patient's vein.

A hollow extension channel 22 at the opposite distal end of the body 12 is provided with external LUER LOK threading 24. A recess 26 is formed at the distal end of the catheter retainer body 12 for retaining a silicone gasket 28 with a closeable hole or slit 30 in the center thereof for receiving the introducer needle 44. This silicone gasket 28 forms a fluid tight seal when the needle 44 is withdrawn.

Optionally a ring 31 is secured over the outer end of gasket 28 in recess 29 and is formed with a target guide 33 to facilitate insertion of the introducer needle 44 in the slit 30 of the gasket 28.

Metal ring 35 is provided to further aid in tactile guidance. It has aperture 37 for needle 44 and feelers 39.

Needle 44 has a beveled or chiseled point 46 for facilitating insertion in the patient. The other end 50 of the needle 44 is secured in plastic tube collar 52 having dogs 64 and 66 at the distal end 56 thereof. The plastic tube 52 is carried within the internal channel of the hollow cylindrical body 32 which has wings 34 and 36 to facilitate insertion of the needle 44 in the patient.

The cylindrical body 34 has a proximal end opening 42 and a distal opening 40. A sealing gasket 38 is located at distal end 40 to enclose or trap needle 44 upon withdrawal.

The end 56 of the tube 52 has a curved transparent tubing 68 fitted over it which is curved at 70. It serves as a blood sighting means indicating that the needle 44 has penetrated the patient's vein 102. The end 71 of the tubing 68 is provided with a filter valve 72 which allows air to pass, but will not allow fluids such as blood to be transmitted therethrough.

The filter valve 72 is comprised of a hydrophobic filter comprising an air-permeable barrier of a hydrophobic material. Preferably this material is polytetrafluoroethylene having a pore size in the range of 0.2 to 0.5 microns.

The adapter unit 78 of the assembly 2 is comprised of cylindrical body 80 having a hollow annular shaft 78 which is provided with an internal LUER LOK threads 86. A cylindrical shaft 94 having an internal channel 90 and chisel point 96 extends from the base 88 of the body 78 and is provided with openings 97 on the sidewalls thereof. The shaft 94 is proportioned so that the chisel point 96 will extend into the hollow interior of the body 12 through gasket 28 to place the openings 97 in flow communication with the interior of the body 12. Extending from the base 88 of the shaft 94 is the cylindrical shaft 82 over which is slipped the IV tubing 88. The outer end of shaft 82 has nubs 84 which engage LUER LOK threads on the interior of the cap 74. The cap 74 has wings 76 to facilitate turning.

In use, the needle 44 is slipped through the catheter 4 in the position as shown in FIG. 2 and inserted into the patients arm 100, penetrating the desired vein 102. The needle 44 is then withdrawn from the catheter 4 using the winged body 34 in conjunction with the plate 35 as guides. As the introducer 44 needle is removed from the gasket 28 in the body 12, the opening 30 self seals, cutting off any flow of blood to prevent accidental spillage of blood. After separation from body 12, the needle 44 is then withdrawn into the body 32 by pulling on the curved tube 70. The dogs engage the rear wall 43 at the end 42 in the body 32, retaining the needle 44 safely therein to prevent accidental needle pricks.

The adapter 78 is then fitted to the end of an IV tubing 88. The chisel point 96 penetrates the gasket 28 as the body 80 is turned on to the thread 24 as shown in FIG. 5.

The assembly of the invention thus allows the safe insertion of a catheter and withdrawal of the insertion needle into a safe body to prevent accidental pricking, while at the same time, preventing any backflow of blood through the catheter assembly and protecting the technician or the nurse. The IV tubing is safely hooked up again without possibility of spillage of blood.

While the invention has been described by reference to an illustrative embodiment, it is not intended that the novel device be limited thereby, but that modifications thereof are intended to be included as falling within the broad spirit and scope of the foregoing disclosure, the following claims and the appended drawings.

What is claimed is:

1. A catheter assembly comprising a catheter of flexible plastic tubing secured at one end to a catheter hub, a hollow adaptor body with a distal end for fluid tight connection to said catheter hub and in fluid communication therewith, the proximal end of said adaptor body having a self-closing elastomeric gasket valve member, an introducer needle proportioned so as the sharpened distal end thereof penetrates said gasket valve member and when in extended position extends through said hollow catheter body, hub, and catheter tubing for penetration of a patient's vein to introduce said catheter into said vein, the proximal end of said introducer needle secured in flow communication to a plastic collar having a distal and proximal end, and slidable within a hollow cylindrical container, said collar having dogs at the proximal end thereof to engage the rear wall of said cylindrical container to stop rearward movement, a sealable gasket closure at the distal end of cylindrical container to safely enclose the sharp end of said introducer needle within said cylindrical container upon withdrawal, a curved transparent plastic tube extending from the proximal end of said plastic collar for sighting blood flash back, said tube having a filter valve in the end thereof to allow passage of air, but preclude passage of liquids, and an adaptor unit connectable to said adaptor body, said adapter unit having a hollow shaft at its distal end, said hollow shaft having a sharp end, and ports on its side walls said hollow shaft proportioned to pierce said gasket valve member in said adaptor body to place said adaptor body and said adapter unit in flow communication, the proximal end of said adapter unit adapted to be connected in flow communication with IV tubing.

2. An assembly as claimed in claim 1 wherein said cylindrical body has lateral wings thereon.

* * * * *